(12) United States Patent
Rao et al.

(10) Patent No.: US 8,912,337 B2
(45) Date of Patent: Dec. 16, 2014

(54) SALTS AND POLYMORPHS OF DEXRABEPRAZOLE

(75) Inventors: Dharmaraj Ramachandra Rao, Maharashtra (IN); Rajendra Narayanrao Kankan, Maharashtra (IN); Srinivas Laxminarayan Pathi, Bangalore (IN); Dilip Ramdas Birari, Maharashtra (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 13/805,235

(22) PCT Filed: Jun. 24, 2011

(86) PCT No.: PCT/GB2011/000957
§ 371 (c)(1),
(2), (4) Date: Mar. 1, 2013

(87) PCT Pub. No.: WO2011/161421
PCT Pub. Date: Dec. 29, 2011

(65) Prior Publication Data
US 2013/0150588 A1    Jun. 13, 2013

(30) Foreign Application Priority Data
Jun. 24, 2010   (IN) .................. 1868/MUM/2010

(51) Int. Cl.
*A61K 31/44*   (2006.01)
*C07D 401/00*  (2006.01)
*C07D 401/12*  (2006.01)

(52) U.S. Cl.
CPC .................................. *C07D 401/12* (2013.01)
USPC ....................................... 546/273.7; 514/338

(58) Field of Classification Search
None
See application file for complete search history.

(56) References Cited

U.S. PATENT DOCUMENTS

2007/0026071 A1    2/2007  Namburi et al.

FOREIGN PATENT DOCUMENTS

| CN | 101250183 A | * | 8/2008 |
| CN | 101343266 A | | 1/2009 |
| CN | 101766613 A | | 7/2010 |
| EP | 0773940 A1 | | 5/1997 |
| WO | 9602535 A1 | | 2/1996 |
| WO | 9955157 A1 | | 11/1999 |
| WO | 9955158 A1 | | 11/1999 |
| WO | 0104109 A1 | | 1/2001 |
| WO | 2004060263 A2 | | 7/2004 |
| WO | 2005082888 A1 | | 9/2005 |
| WO | 2007041790 A1 | | 4/2007 |
| WO | 2011161421 A1 | | 12/2011 |

OTHER PUBLICATIONS

Brittain, H., ed Polymorphism in Pharmaceutical Solids 2009 pp. 318-335.*
Ivanisevic, I. Pharm. Form. Qual. 2011, pp. 30-33.*
Foreign communication from a related counterpart application—International Search Report and Written Opinion, PCT/GB2011/000957 dated Sep. 7, 2011, 12 pages.
Nochi, Shigeharu, et al., "Preparation and Absolute Configurations of Optical Isomers of Sodium 2-[[4-(3-Methoxypropoxy)-3-methylpyridin-2-yl]methylsulfinyl]-1H-benzimidazole (E3810)", Chem. Pharm. Bull., 1996, pp. 1853-1857, vol. 40, No. 10, Pharmaceutical Society of Japan.
Foreign communication from a related counterpart application—International Preliminary Report on Patentability, PCT/GB2011/000957 dated Dec. 28, 2012, 8 pages.

* cited by examiner

*Primary Examiner* — Heidi Reese
(74) *Attorney, Agent, or Firm* — Conley Rose, P.C.; Rodney B. Carroll (57) ABSTRACT

The present invention provides dexrabeprazole magnesium hydrate and a process for its preparation. The present invention also provides a magnesium, calcium or potassium salt of dexrabeprazole, optionally in amorphous form, and processes for its preparation.

22 Claims, 3 Drawing Sheets

SALTS AND POLYMORPHS OF DEXRABEPRAZOLE

CROSS-REFERENCE TO RELATED APPLICATIONS

This application is a filing under 35 U.S.C. 371 of International Application No. PCT/GB2011/000957 filed Jun. 24, 2011, entitled "Salts and Polymorphs of Dexrabeprazole," which claims priority to Indian Patent Application No. 1868/MUM/2010 filed on Jun. 24, 2010, which applications are incorporated by reference herein in their entirety.

TECHNICAL FIELD OF THE INVENTION

The present invention relates to novel salts and hydrates of dexrabeprazole.

BACKGROUND OF THE INVENTION

Racemic rabeprazole is chemically known as 2-[[[4-(3-methoxypropoxy)-3-methyl-2-pyridinyl]methyl]sulfinyl]-1H-benzimidazole and is represented as follows:

EP0773940 describes the preparation of R-(+)-rabeprazole and S-(−)-rabeprazole. Separation of racemic rabeprazole into R-(+)-rabeprazole and S-(−)-rabeprazole by chromatography has been described by Nochi et al in Chem. Pharm. Bull. 44, 1853-1857 (1996). Dexrabeprazole is known as R-rabeprazole.

WO9955157 and WO9955158 describe various formulations of R-(+)-rabeprazole and S-(−)-rabeprazole, respectively.

Various salts such as calcium, sodium, zinc and nitrate of racemic rabeprazole have been disclosed in different patents. WO0104109 claims Li, Na, K, Mg, Ca, Ti and quaternary ammonium salt of racemic rabeprazole. The most commonly-used salt of racemic rabeprazole is the sodium salt.

WO2007041790 and WO2004060263 simply mention the existence of the isomers of rabeprazole while describing the magnesium salt of rabeprazole. Neither of these applications discloses examples of the preparation of the magnesium salt of dexrabeprazole.

The sodium salt of dexrabeprazole is known and available commercially. However, the sodium salt of dexrabeprazole is not stable over a long period of time. Also it is hygroscopic in nature. This makes the storage and handling of the dexrabeprazole sodium difficult and also it is further difficult to formulate dexrabeprazole sodium in a suitable dosage form.

Hence, there was a need to develop a stable salt of dexrabeprazole which can be stored as well as easily formulated into dosage form.

SUMMARY OF THE INVENTION

According to a first aspect of the present invention, there is provided dexrabeprazole magnesium hydrate.

In an embodiment, dexrabeprazole magnesium hydrate has a water content ranging from about 8% w/w to about 11% w/w. Typically, the water content ranges from about 9% w/w to about 11% w/w, preferably from about 9.5% w/w to about 10.5% w/w.

Figure 1:
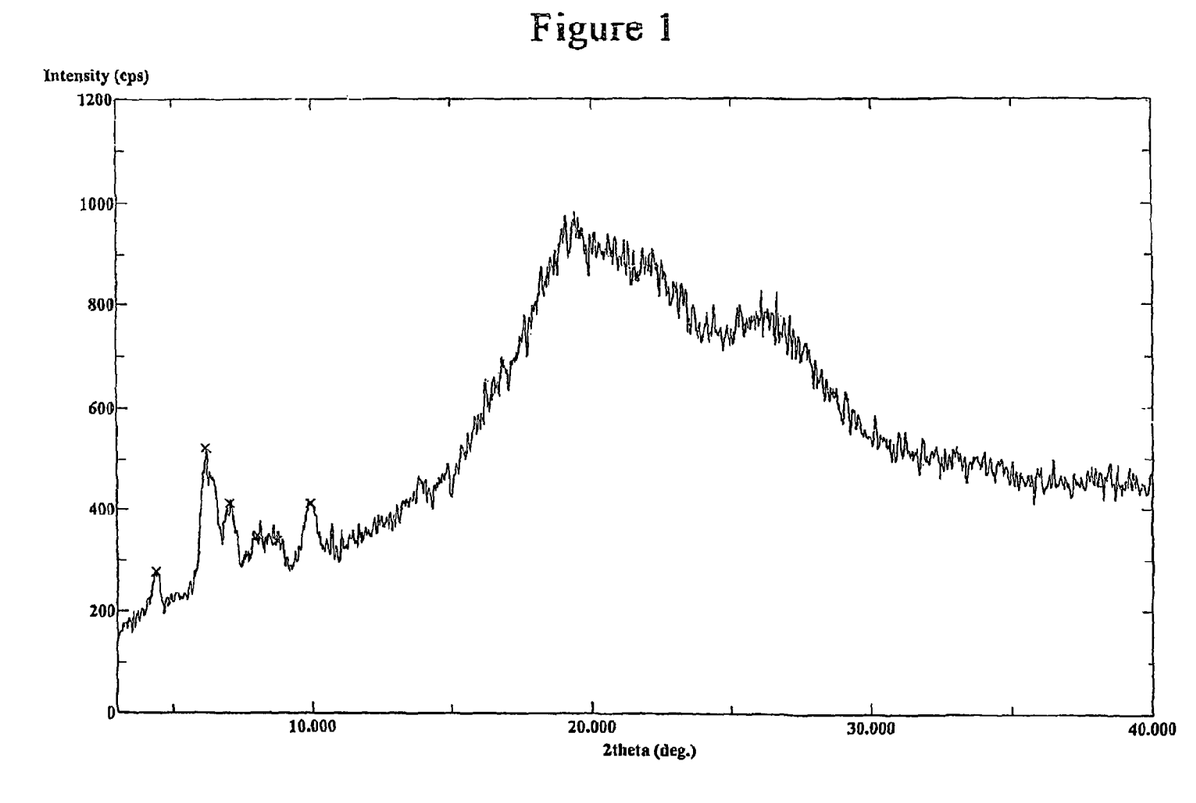
FIG. 1 depicts an X-ray diffraction pattern of crystalline dexrabeprazole magnesium hydrate.
Figure 2:
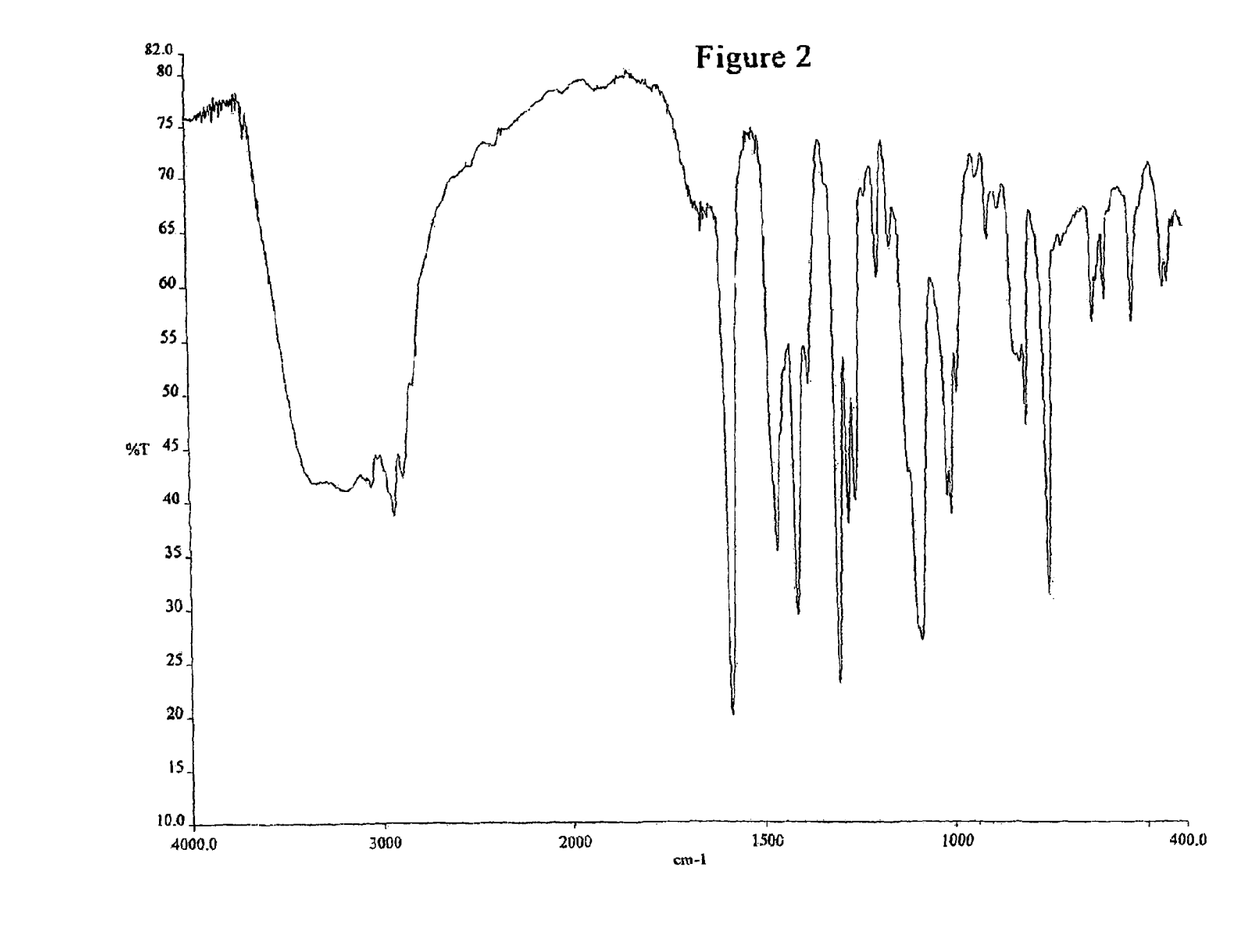
FIG. 2 depicts an Infra-red absorption spectrum of crystalline dexrabeprazole magnesium hydrate.

The dexrabeprazole magnesium hydrate may be in crystalline form. Crystalline dexrabeprazole magnesium hydrate may be characterized by having an X-ray diffraction pattern with peaks at 4.3°, 6.2° and 9.9°2θ±0.2° 2θ. Crystalline dexrabeprazole magnesium hydrate may be characterized by having an XRPD pattern as shown in FIG. 1. Crystalline magnesium salt of dexrabeprazole may be characterized by having an IR pattern as shown in FIG. 2.

According to another aspect of the present invention, there is provided, a process for the preparation of dexrabeprazole magnesium hydrate. The process comprises reacting dexrabeprazole or a salt thereof with an alcoholic solution of magnesium chloride. In an embodiment, the process comprises reacting dexrabeprazole potassium with an alcoholic solution of magnesium chloride. Suitably, the alcohol is methanol. Optionally, the magnesium chloride is in the form of magnesium chloride hexahydrate. Most preferably, the process comprises reacting potassium with a methanolic solution of magnesium chloride hexahydrate.

In an embodiment, the process comprises forming a reaction mass comprising the dexrabeprazole or salt thereof and alcoholic magnesium chloride; filtering the reaction mass; adding an organic solvent to the filtrate; and isolating the dexrabeprazole magnesium hydrate. In an embodiment, the process comprises stirring a solution of the dexrabeprazole or salt thereof and an alcoholic magnesium chloride at a temperature ranging from 20° C. to 25° C.; cooling the solution to a temperature ranging from 0° C. to 5° C.; filtering the solution; adding an organic solvent to the filtrate; stifling the solution at a temperature ranging from 20° C. to 25° C.; cooling the solution to a temperature ranging from 0° C. to 5° C.; filtering the solution; and drying under vacuum.

In an embodiment, the organic solvent is selected from water, methanol, ethanol, isopropanol, methylene chloride, toluene, hexane, diisopropyl ether or a mixture thereof. Preferably, the organic solvent is diisopropyl ether.

In an embodiment, the process comprises contacting 2-[[[4-(3-methoxypropoxy)-3-methyl-2-pyridinyl]methyl]thio]-1H-benzimidazole (rabeprazole sulfide) with a chiral reagent in an organic solvent and water followed by addition of titanium isopropoxide. A base is added to this reaction mass followed by an oxidizing agent to obtain dexrabeprazole. The so-obtained dexrabeprazole may then be reacted with the alcoholic solution of magnesium chloride to form dexrabeprazole magnesium hydrate. Alternatively, the dexrabeprazole obtained after reaction with the oxidizing agent is converted to a salt, suitably the potassium salt, and the salt of dexrabeprazole is reacted with the alcoholic solution of magnesium chloride to form dexrabeprazole magnesium hydrate.

In an embodiment, the reaction mass is heated to a temperature ranging from 45° C. to 60° C. after addition of titanium isopropoxide.

In an embodiment, the base is added at a temperature ranging from 40° to 50° C.

In an embodiment, the oxidation is carried out at temperature ranging from −20 to 10° C.

According to another aspect of the present invention, there is provided magnesium, calcium and potassium salts of dexrabeprazole. As noted above, the preparation of a magnesium salt of dexrabeprazole is not explicitly disclosed, nor exemplified in WO2007041790 and WO2004060263. Further the known sodium salt of dexrabeprazole is disadvantageous in terms of inter alia storage and hygroscopicity.

In an embodiment, there is provided dexrabeprazole magnesium. The salt is in the form of dexrabeprazole hemimagnesium, i.e. around 2 moles of dexrabeprazole anion to around 1 mole of magnesium cation.

In an embodiment, there is provided dexrabeprazole calcium. The salt is in the form of dexrabeprazole hemicalcium, i.e. around 2 moles of dexrabeprazole anion to around 1 mole of calcium cation.

In an embodiment, there is provided dexrabeprazole potassium, i.e. around 1 mole of dexrabeprazole anion to 1 mole of potassium cation.

According to another aspect of the present invention, there is provided a process for the preparation of a magnesium, calcium or potassium salt of dexrabeprazole. The process comprises contacting dexrabeprazole with a magnesium or calcium or potassium salt in an organic solvent.

Optionally, the process is carried out in the presence of an organic or inorganic base, the base is selected from monomethyl amine, triethyl amine, N,N-diisopropyl ethyl amine, pyridine, morpholine, sodium carbonate, potassium carbonate, sodium bicarbonate, potassium bicarbonate, potassium hydroxide, sodium hydroxide and lithium hydroxide.

In an embodiment, the dexrabeprazole is prepared by: i) contacting 2-[[[4-(3-methoxypropoxy)-3-methyl-2-pyridinyl]methyl]thio]-1H-benzimidazole with a chiral titanium complex in an organic solvent; and ii) adding a base and an oxidizing agent.

According to another aspect of the present invention, there is provided a salt of dexrabeprazole in amorphous form.

According to another aspect of the present invention, there is provided a process for the preparation of an amorphous salt of dexrabeprazole. The process comprises addition of an inorganic base or a salt of magnesium, calcium or potassium to dexrabeprazole or a salt thereof in a solvent to form a solution and isolation of the magnesium, calcium or potassium salt of dexrabeprazole in amorphous form.

In an embodiment, the solution is heated to a temperature ranging from 35° C. to 50° C., and the isolation comprises filtration and drying under vacuum at a temperature ranging from 20° C. to 30° C.

In an embodiment, the inorganic base or salt of magnesium, calcium or potassium are added to dexrabeprazole.

In an embodiment, the base or inorganic salt of magnesium, calcium or potassium are added to dexrabeprazole sodium.

In an embodiment, the process comprises contacting 2-[[[4-(3-methoxypropoxy)-3-methyl-2-pyridinyl]methyl]thio]-1H-benzimidazole with a chiral titanium complex in an organic solvent followed by oxidation using an oxidizing agent and a base to obtain dexrabeprazole. Dexrabeprazole is then treated with an inorganic base or a salt to obtain the corresponding dexrabeprazole salt in a suitable solvent or mixture of solvents, the product is isolated by filtration and dried to obtain amorphous salt of dexrabeprazole.

In an embodiment, the 2-[[[4-(3-methoxypropoxy)-3-methyl-2-pyridinyl]methyl]thio]-1H-benzimidazole is added at a temperature ranging from 45° C. to 75° C., preferably from 50° to 60° C.

In an embodiment, the base and oxidizing agent are added at a temperature ranging from 25° C. to 35° C., preferably from 28° to 32° C.

In an embodiment, the chiral titanium complex is prepared using a chiral ligand. In an embodiment, the chiral ligand is (+) diethyl-L-tartrate.

In an embodiment, the oxidizing agent is selected from hydrogen peroxide, cumene hydroperoxide, tert.butyl hydorperoxide, peracetic acid, m-chloro perbenzoic acid, sodium hypochlorite and sodium hypobromite, preferably cumene hydroperoxide.

According to another aspect of the present invention, there is provided a pharmaceutical composition comprising dexrabeprazole or a salt or hydrate thereof as described above (particularly dexrabeprazole magnesium hydrate) together with one or more pharmaceutically acceptable excipients.

According to another aspect of the present invention, there is provided dexrabeprazole or a salt or hydrate thereof as described above (particularly dexrabeprazole magnesium hydrate) for use in medicine.

According to another aspect of the present invention, there is provided the use of dexrabeprazole or a salt or hydrate thereof as described above (particularly dexrabeprazole magnesium hydrate) in the manufacture of a medicament for treating ulcers.

According to another aspect of the present invention, there is provided a method of treating ulcers comprising administering to a patient in need thereof an effective amount of dexrabeprazole or a salt or hydrate thereof as described above (particularly dexrabeprazole magnesium hydrate).

DETAILED DESCRIPTION OF THE INVENTION

The present invention provides magnesium, calcium and potassium salts of dexrabeprazole.

Dexrabeprazole magnesium and calcium are hemimagnesium and hemicalcium salts containing 2 moles of dexrabeprazole anion to 1 mole of magnesium and calcium cation respectively.

Dexrabeprazole potassium contains 1 mole of dexrabeprazole anion to 1 mole of potassium cation.

In another aspect of the present invention, there is provided a process for the preparation of magnesium, calcium and potassium salts of dexrabeprazole. The process comprises contacting dexrabeprazole with magnesium, calcium or potassium salt in a suitable organic solvent.

Optionally the process is carried out in presence of a base. The base may be selected from an organic or an inorganic base.

The inorganic base may be selected from: an alkali metal carbonate (for example sodium carbonate and potassium carbonate); an alkali metal bicarbonate (for example sodium bicarbonate and potassium bicarbonate); and an alkali metal hydroxide (for example potassium hydroxide, sodium hydroxide and lithium hydroxide).

The organic base may be selected from monomethyl amine, triethyl amine, N,N-diisopropyl ethyl amine, pyridine and morpholine.

The salt of magnesium, calcium or potassium may be an organic or inorganic salt. Suitably, the salt is the chloride, nitrate, sulphate, phosphate, carbonate, oxalate, tartrate, acetate, succinate, lactate or formate salt.

The organic solvent for preparation of the salt may be selected from water, ethanol, methanol, butanol, isopropanol, methylene chloride, ethylene chloride, chloroform, ethyl acetate, methyl acetate, butyl acetate, acetone, ethyl methyl ketone, methyl isobutyl ketone, diethyl carbonate, tert.butyl methyl ether, diisopropyl ether, dioxane, tetrahydrofuran, toluene, acetonitrile or mixtures thereof.

It has been observed that the sodium salt of dexrabeprazole is not stable on storage. It degrades and also absorbs moisture on storage. This further makes it difficult to prepare a stable formulation using dexrabeprazole sodium. Now it has been found that the magnesium salt, specifically in a hydrate form, is more stable and has advantageous properties compared to the sodium salt and hence, is well suited for formulating in a suitable dosage form. This is illustrated below.

Magnesium and sodium salts of dexrabeprazole were kept on stability at 2° C. to 8° C. for 6 months and were studied for water content and impurity profile and it was found that dexrabeprazole sodium absorbed more water than dexrabeprazole magnesium. Also dexrabeprazole magnesium does not show significant rise in impurities as compared to dexrabeprazole sodium. Water content was measured using about 0.2 g sample in methanol by KF Autotitrator.

| Properties | dexrabeprazole magnesium hydrate | | dexrabeprazole sodium | |
|---|---|---|---|---|
| | Initial | At 6 months | Initial | At 6 months |
| Water content (% w/w) | 10.27 | 10.46 | 6.84 | 13.58 |
| Impurities | | | | |
| Impurity A (%) | 0.02 | 0.02 | 0.02 | 0.06 |
| Impurity B (%) | 0.07 | 0.07 | 0.87 | 1.25 |
| Impurity C (%) | 0.09 | 0.09 | 0.22 | 0.33 |

These results indicate that dexrabeprazole magnesium in a hydrate form is advantageous compared to dexrabeprazole sodium.

In another embodiment of the present invention, there is provided crystalline dexrabeprazole magnesium hydrate. The molar ratio of dexrabeprazole to magnesium is 2:1.

Further, the crystalline form of dexrabeprazole magnesium hydrate is in a partially crystalline form as characterized by having an XRD pattern as shown in FIG. 1.

Crystalline dexrabeprazole magnesium hydrate is characterized by having an IR pattern as shown in FIG. 2.

Crystalline dexrabeprazole magnesium has a water content in the range of about 8% to about 11%.

The XRPD of the crystalline dexrabeprazole magnesium was measured on a Rigaku Dmax 2200 X-ray powder diffractometer using a Cu $K_\alpha$ radiation source and is characterized by its XRPD pattern as shown in FIG. 1. The XRPD measurement parameters were as follows:
1. Temperature: Ambient temperature
2. X-ray wavelength: 1.5405 A°
3. Anode material(Source): Cu Kα

The IR spectrum of the crystalline dexrabeprazole magnesium is shown in FIG. 2. The IR measurement was by potassium bromide dispersion by FTIR.

The crystalline dexrabeprazole magnesium hydrate may be characterized by having an XRPD pattern comprising peaks at 4.3°, 6.2°, 9.9° 2θ (±0.2° 2θ).

In another aspect of the present invention, there is provided a process for the preparation of crystalline dexrabeprazole magnesium hydrate. The process comprises contacting 2-[[[4-(3-methoxypropoxy)-3-methyl-2-pyridinyl]methyl]thio]-1H-benzimidazole with a chiral reagent in an organic solvent and water followed by addition of titanium isopropoxide. The base is added to this reaction mass followed by an oxidizing agent to obtain dexrabeprazole. The so obtained dexrabeprazole is then treated with suitable inorganic salt of magnesium to obtain corresponding dexrabeprazole magnesium salt. This magnesium salt is optionally purified from a suitable organic solvent. In an embodiment, the dexrabeprazole magnesium hydrate is in crystalline form, and the preparation of the crystalline form comprises reacting the dexrabeprazole with an alcoholic (preferably methanolic) solution of magnesium chloride.

Optionally, dexrabeprazole is converted into a first salt and then from the first salt to a second salt.

The chiral reagent used may be selected from dimethyl (+) or (−) tartrate, diethyl (+) or (−) tartrate, or (+) or (−) naphthol. The preferred chiral reagent is diethyl (+)tartrate.

The organic solvent for oxidation may be selected from methylene chloride, toluene, ethyl acetate, methyl ethyl ketone, methyl isobutyl ketone, diethyl carbonate and tetrahydrofuran. The preferred solvent is toluene.

After addition of titanium isopropoxide, the reaction mass is typically heated to a temperature ranging from about 45° C. to about 60° C., preferably to a temperature of about 50° C. to 55° C.

The base used may be the same as described above for the preparation of the salt of dexrabeprazole.

Addition of base is typically carried out at a temperature ranging from about 40° C. to about 50° C., preferably at around 43° C.

The oxidizing agent used for the asymmetric oxidation may be selected from hydrogen peroxide, cumene hydroperoxide, tert.butyl hydroperoxide, peracetic acid, m-chloro perbenzoic acid, sodium hypochlorite and sodium hypobromite, preferably cumene hydroperoxide.

Oxidation is typically carried out at a lower temperature ranging from −20 to 10° C., preferably at −5 to -15° C.

The salt of magnesium used for preparation of dexrabeprazole magnesium may be the same as that described above for the preparation of the salt of dexrabeprazole.

The organic solvent used for purification may be selected from water, methanol, ethanol, isopropanol, methylene chloride, toluene, hexane, diisopropyl ether or mixtures thereof.

In another aspect of the present invention, there is provided a salt of dexrabeprazole in amorphous form.

Figure 3:
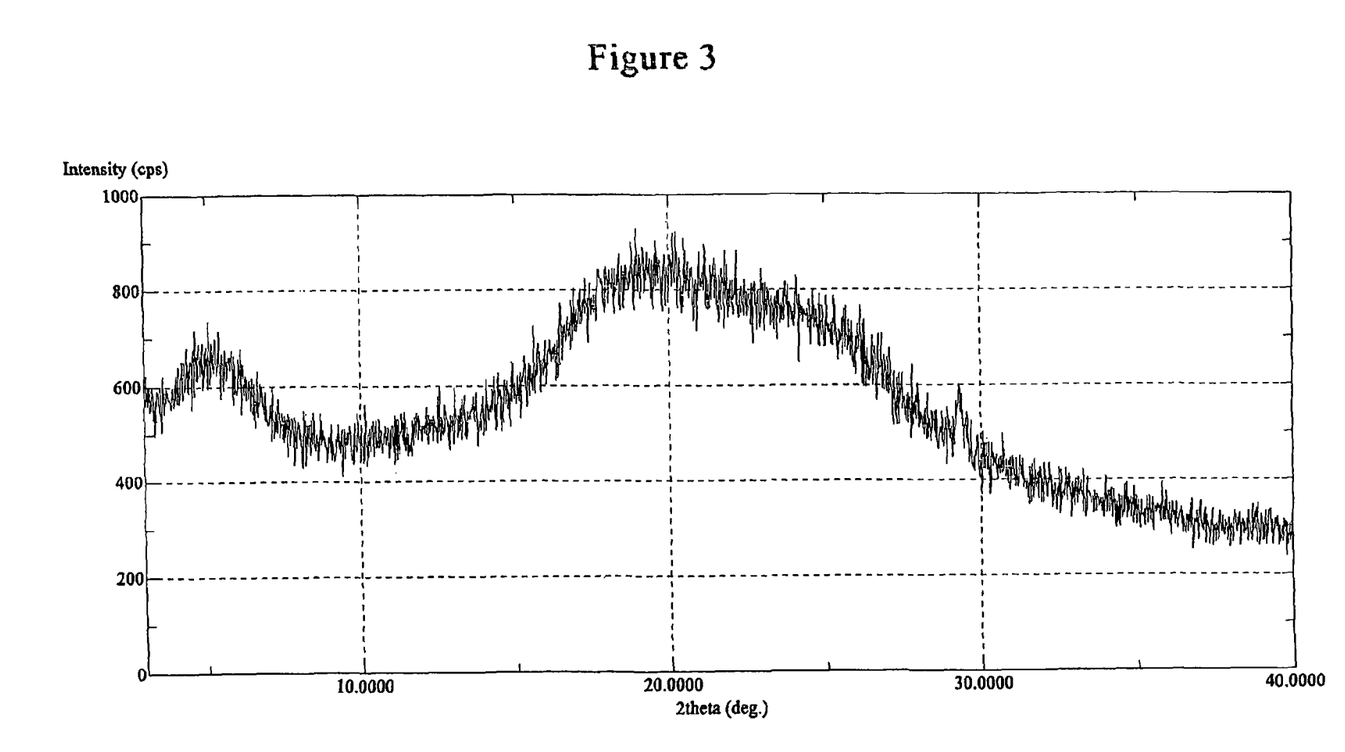
FIG. 3 depicts an X-ray diffraction pattern of amorphous dexrabeprazole calcium.

Amorphous dexrabeprazole potassium and magnesium are characterized by XRPD patterns showing no sharp peaks as depicted in FIG. 3 for the calcium salt.

In another aspect of the present invention, there is provided a process for the preparation of an amorphous salt of dexrabeprazole. The process comprises contacting 2-[[[4-(3-methoxypropoxy)-3-methyl-2-pyridinyl]methyl]thio]-1H-benzimidazole with a chiral titanium complex in an organic solvent followed by addition of a base and then a suitable oxidizing agent to obtain dexrabeprazole. Dexrabeprazole is treated with a suitable inorganic salt or a base in a suitable solvent or mixture of solvents to obtain the corresponding dexrabeprazole salt. The product is isolated, suitably by filtration and drying, to obtain an amorphous salt of dexrabeprazole.

In an embodiment, 2-[[[4-(3-methoxypropoxy)-3-methyl-2-pyridinyl]methyl]thio]-1H-benzimidazole is added at an elevated temperature ranging from about 45° C. to about 75° C., preferably from about 50° C. to about 60° C.

In an embodiment, the base and oxidizing agent are added at a temperature ranging from about 25° C. to about 35° C., preferably around 28° C. to 32° C.

Oxidation is carried out in an organic solvent which may be selected from methylene chloride, toluene, ethyl acetate, methyl ethyl ketone, methyl isobutyl ketone, diethyl carbonate and tetrahydrofuran. The preferred solvent is toluene.

The oxidizing agent used for the asymmetric oxidation may be selected from hydrogen peroxide, cumene hydroperoxide, tert.butyl hydroperoxide, peracetic acid, m-chloroperbenzoic acid, sodium hypochlorite and sodium hypobromite, preferably cumene hydroperoxide.

The chiral titanium complex is formed by the known processes using a chiral ligand (for example (+)-diethyl-L-tartrate) and a titanium (IV) compound (for example titanium alkoxide), preferably titanium isopropoxide. The preferred chiral ligand is (+)-diethyl-L-tartrate.

The base used may be selected from an organic or inorganic base.

The inorganic base may be selected from sodium carbonate, potassium carbonate, potassium hydroxide, sodium hydroxide and lithium hydroxide. The organic base may be selected from monoethanol amine, triethyl amine and N,N-diisopropyl ethyl amine. The preferred base used for the reaction is N,N-diisopropyl ethyl amine.

The organic solvent used for oxidation may be the same as described for preparation of crystalline dexrabeprazole magnesium hydrate.

The dexrabeprazole obtained is further converted into a salt by treatment with a suitable inorganic base or a salt in a suitable organic solvent. Optionally, this reaction mixture is heated to dissolve the contents.

The inorganic salt used for preparation of the salt of dexrabeprazole may be selected from calcium chloride, magnesium chloride, potassium chloride, calcium acetate, magnesium acetate and potassium acetate. The inorganic base may be selected from sodium hydroxide, magnesium hydroxide, calcium hydroxide, lithium hydroxide and potassium hydroxide.

The solvent used for preparation of the amorphous salt of dexrabeprazole may be selected from water, methanol, methyl isobutyl ketone, acetone, ethyl methyl ketone, acetonitrile, tetrahydrofuran or mixtures thereof.

Further, the dexrabeprazole salt obtained may be converted into another salt by the process described above.

EXAMPLES

The details of the invention are given in the examples which are provided below for illustration only and therefore these examples should not be construed to limit the scope of the invention.

Example 1

Preparation of Dexrabeprazole Magnesium 15 g of dexrabeprazole was stirred in 75 ml water and heated to obtain a clear solution. 25 ml magnesium chloride hexahydrate (1M) was added dropwise and stirred for 6 hours at 25° C. The precipitated solid was filtered, washed with 30 ml water and dried under vacuum at 25° C. for 15 hours.

Yield: 11.0 g

Example 2

Preparation of Crystalline Dexrabeprazole Magnesium Hydrate

Toluene (500 ml) was charged into the reaction flask and nitrogen blanket was started. (+)-diethyl tartrate (18 g), water (0.25 g) and 2-[[[4-(3-methoxypropoxy)-3-methyl-2-pyridinyl]methyl]thio]-1H-benzimidazole (rabeprazole sulphide) (50 g) were further charged and stirred for 15 minutes at 23±2° C. Titanium (IV) isopropoxide (10.35 g) was added to the reaction mass followed by heating to 50-55° C. and the reaction was maintained for 30 minutes.

The reaction mass was then slowly cooled to 43±2° C., diisopropyl ethyl amine (10 ml) was added to it and reaction mass was then chilled to −10±2° C. 82 g of cumene hydroperoxide diluted with 150 ml of toluene was added to the reaction mass at −10±2° C. and stirred for 4-4½ hours. After completion of the reaction, reaction mass was quenched with 500 ml of 2% sodium thiosulphate solution. 150 ml of 20% sodium hydroxide solution was charged at less than 0° C. and the temperature was raised to 20±2° C. The layers were separated and the aqueous layer was washed with 750 ml of toluene. The aqueous layer was clarified and further washed with 750 ml of toluene. pH of the aqueous layer was adjusted to 9.5±0.2 using aqueous ammonium acetate solution, extracted with 750 ml of methylene chloride and then methanolic potassium hydroxide solution (7.5 g dissolved in 200 ml of methanol) was added to methylene chloride layer. The aqueous layer was extracted twice with 500 ml of methylene chloride, dried and the combined layer was then concentrated under vacuum at 30±2° C. and replaced with 25 ml of methanol. The residue was dissolved in 750 ml of methanol.

11 g of magnesium chloride hexahydrate was dissolved in 250 ml of methanol and the solution of dexrabeprazole potassium obtained above was added to this at 23±2° C. The mixture was stirred for 1 hour, chilled to 0-5° C., filtered over hyflo and washed with 50 ml of methanol. The clear filtrate was concentrated to about 150 ml to which 500 ml of diisopropyl ether was charged and stirred for 1 hour at 23±2° C. The reaction mass was chilled to 0-5° C., filtered, washed with diisopropyl ether and slurried in water. The reaction mass was again filtered, washed with water. The material was slurried in 10% isopropyl alcohol in water followed by filtration and washing with water. The product was dried at 35±1° C. under vacuum for 12 hours.

Yield: 35 g (water content: 10.27%)

Example 3

Preparation of Dexrabeprazole Potassium

Toluene (1000 ml) was charged into reaction flask assembly under nitrogen blanket. To this (+)-diethyl tartrate (36 g), water (0.5 g) and 2-[[[4-(3-methoxypropoxy)-3-methyl-2-pyridinyl]methyl]thio]-1H-benzimidazole (100 g) were charged and stirred for 15 minutes at 23±2° C. Titanium (IV) isopropoxide (20.70 g) was added to the reaction mass, heated to 50-55° C. and maintained for 30 minutes. The reaction mass was then slowly cooled to 43±2° C., diisopropyl ethyl amine (20 ml) was added to it and the reaction mass and then chilled to −10±2° C. 164 g of cumene hydroperoxide diluted with 300 ml of toluene was added to the reaction mass at −10±2° C. and stirred for 4-4½ hours. After completion of the reaction, reaction mass was quenched with 1000 ml of 2% sodium thiosulphate solution. 300 ml of 20% sodium hydroxide solution was charged below 0° C. and the temperature was raised to 20±2° C. The layers were separated and the aqueous layer was washed with 1500 ml of toluene. The aqueous layer was clarified and further washed with 1500 ml of toluene. pH of the aqueous layer was adjusted to 9.5±0.2 using aqueous ammonium acetate solution, extracted with 1500 ml of methylene chloride and then methanolic potassium hydroxide solution (15 g dissolved in 400 ml of methanol) was added to methylene chloride layer. Further the aqueous layer was extracted twice with 1000 ml of methylene chloride, dried and the combined methylene chloride layer was then concentrated under vacuum at 30±2° C. to residue and replaced with 50 ml of methanol. 1000 ml of diisopropyl ether was added, stirred, filtered the solid obtained and washed with diisopropyl ether under Nitrogen atmosphere.

Yield: 88.5 g

Example 4

Preparation of Dexrabeprazole Magnesium Hydrate 21.65 g of magnesium chloride hexahydrate was dissolved in 500 ml of methanol and methanolic solution of dexrabeprazole potassium (88.5 g obtained from example 4 was dissolved in 885 ml of methanol) was added to this at 23±2° C. The mixture was stirred for 1 hour at 23±2° C., chilled to 0-5° C., filtered over hyflo and washed with 100 ml of methanol. The clear filtrate was concentrated to about 300 ml to which 885 ml of diisopropyl ether was charged and stirred for 1 hour at 23±2° C. The reaction mass was chilled to 0-5° C., filtered, washed with diisopropyl ether and slurried in water. The reaction mass was again filtered, washed with water. The material was slurried in 10% isopropyl alcohol in water followed by filtration and washing with water. The product was dried at 35±1° C. under vacuum for 12 hours.

Yield: 68.55 g (water content: 9.85%).

Example 5

Preparation of Dexrabeprazole Magnesium Hydrate

Methanolic magnesium chloride hexahydrate solution was prepared by dissolving 5.5 g of magnesium chloride hexahydrate in 125 ml of methanol. 25 g of dexrabeprazole dissolved in 375 ml methanol was added to methanolic magnesium chloride hexahydrate solution at 23±2° C. The mixture was stirred for 1 hour, chilled to 0-5° C., filtered over hyflo and washed with 25 ml of methanol. The clear filtrate was concentrated to about 150 ml to which 250 ml of diisopropyl ether was charged and stirred for 1 hour at 23±2° C. The reaction mass was chilled to 0-5° C., filtered, washed with 75 ml of diisopropyl ether and slurried in water. The reaction mass was again filtered, washed with water. The material was slurried in 10% isopropyl alcohol in water followed by filtration and washing with water. The product was dried at 35±1° C. under vacuum for 12 hours.

Yield: 17.18 g (water content: 10.09%).

Example 6

Preparation of Amorphous Dexrabeprazole Sodium 900 ml toluene, (+) diethyl tartrate (36.0 g, 0.174 mol) and Ti (IV) isopropoxide (25.0 g, 0.087 mol) were charged in a reactor at room temperature and stirred for 10 minutes. Water (0.62 ml, 0.034 mol) was added into it in one lot and the temperature was increased to 55-60° C. 2-[[[4-(3-methoxypropoxy)-3-methyl-2-pyridinyl]methyl]thio]-1H-benzimidazole (100.0 g, 0.291 mol) was added along with 100 ml toluene at 55° C. The reaction was maintained at 55° C. for 1.5 hours. The reaction mass was cooled to 28-32° C. and diisopropyl ethylamine (11.26 g, 0.087 mol) was added. The reaction mass was stirred for 15 minutes at the same temperature and 80% cumene hydroperoxide (60.2 g, 0.32 mol) was added drop wise at 28-32° C. Again the reaction mass was stirred at 28-32° C. for 15 hours.

The reaction mass was cooled to 10-15° C. and 1N sodium hydroxide solution was added drop wise to adjust the pH above 13. The layers were separated. Aqueous layer was washed with 200 ml methyl isobutyl ketone and cooled to 5-10° C. The pH was adjusted with 1:1 water acetic acid to 10.1 to 10.2 to precipitate the solid. The stirring maintained at 0-5° C. for 3.0 hours and then filtered, washed with chilled water and the wet cake was stirred in 1000 ml water for 3 hours.

The reaction mass was filtered and dried under vacuum for 5 hours at room temperature (water content 30-35%). The above vacuum dried material was stirred in 150 ml ethyl acetate, cooled to 5-10° C. and maintained for 45 minutes. The solid obtained was filtered and washed with chilled ethyl acetate. The material was dried under vacuum till water content reached to 20-25% to obtain 42 g of dexrabeprazole hydrate.

Dexrabeprazole 42.0 g (water content 20-25%) was stirred in 250 ml methyl isobutyl ketone and 35 ml acetonitrile at room temperature under nitrogen atmosphere and then heated to 40-45° C. to obtain clear solution. This clear solution was treated with 40% sodium hydroxide solution and stirred for 15 hours. The reaction mass was then cooled to 0-5° C. and stirred for 2 hours. The precipitated solid was filtered, washed with 50 ml methyl isobutyl ketone and dried under vacuum at room temperature for 15 hours.

Yield—30 g (water content 5-6%)

Example 7

Preparation of Amorphous Dexrabeprazole Magnesium

Dexrabeprazole 10 g (water content 20-25%) was stirred in 50 ml water at 25° C. and heated to 40-45° C. to obtain clear solution. 14 ml magnesium chloride hexahydrate (1M) was added dropwise and stirred for 5 hours at 25° C. The precipitated solid was filtered, washed with 20 ml water and dried under vacuum at 25° C. for 15 hours.

Yield—7.5 g (water content 7-8%)

Example 8

Preparation of Amorphous Dexrabeprazole Calcium

Dexrabeprazole sodium 5.0 g (water content 8-9%) obtained from above example was stirred along with 25 ml water and heated up to 40-45° C. to obtain clear solution. 6 ml calcium chloride (1M) was added dropwise at 25° C-27° C. and stirred for 3 hours at 25° C. The precipitated solid was filtered, washed with 2.0 vol. water and dried under vacuum at room temperature for 15 hours.

Yield—3.1 g (water content 7-8%)

Example 9

Preparation of Amorphous Dexrabeprazole Magnesium

Dexrabeprazole sodium 5.0 g (water content 8-9%) was stirred along with 25 ml of water and heated up to 40-45° C. to obtain clear solution. 7 ml magnesium chloride hexahydrate (1M) was added dropwise and stirred for 3 hours at 25° C. The precipitated solid was filtered, washed with 10 ml of water and dried under vacuum at room temperature for 15 hours.

Yield—3.7 g (water content 7-8%)

The invention claimed is:

1. Dexrabeprazole magnesium hydrate in partially crystalline form.

2. Dexrabeprazole magnesium hydrate according to claim 1, having a water content ranging from about 9.5% w/w to about 10.5% w/w.

3. Dexrabeprazole magnesium hydrate according to claim 1, in partially crystalline form and being characterized by having an X-ray diffraction pattern with peaks at 4.3°, 6.2° and 9.9° 2θ+/−0.2°2θ.

4. Dexrabeprazole magnesium hydrate according to claim 1, having an X-ray diffraction pattern as shown in FIG. 1.

5. Dexrabeprazole magnesium hydrate according to claim 1, having an IR Spectrum as shown in FIG. 2.

6. A process for preparing dexrabeprazole magnesium hydrate according to claim 1, which process comprises: reacting dexrabeprazole or a salt thereof with an alcoholic solution of magnesium chloride.

7. The process according to claim 6, wherein the process comprises forming a reaction mass comprising the dexrabeprazole or salt thereof and alcoholic magnesium chloride; filtering the reaction mass; adding an organic solvent to the filtrate; and isolating the dexrabeprazole magnesium hydrate.

8. The process according to claim 7, wherein the organic solvent is diisopropyl ether.

9. The process according to claim 6, wherein the dexrabeprazole or salt thereof is prepared by: i) contacting 2-[[[4-(3-methoxypropoxy)-3-methyl-2-pyridinyl]methyl]thio]-1H-benzimidazole with a chiral reagent in an organic solvent; ii) adding water to the reaction mass followed by titanium isopropoxide; iii) adding a base to the reaction mass followed by an oxidizing agent to obtain dexrabeprazole; iv) optionally converting dexrabeprazole to a salt thereof.

10. The process according to claim 9, wherein the dexrabeprazole is converted to a salt thereof and the dexrabeprazole salt is reacted with the alcoholic solution of magnesium chloride.

11. The process according to claim 9, wherein the reaction mass is heated to a temperature ranging from 45° C. to 60° C. after addition of titanium isopropoxide.

12. Dexrabeprazole magnesium hydrate according to claim 2, in partially crystalline form and being characterized by having an X-ray diffraction pattern with peaks at 4.3°, 6.2° and 9.9°2θ+/−0.2°2θ.

13. Dexraboprazole magnesium hydrate according to claim 12, having an X-ray diffraction pattern as shown in FIG. 1.

14. Dexrabernazole magnesium hydrate according to claim 13, having an IR Spectrum as shown in FIG. 2.

15. Dexrabernazole magnesium hydrate according to claim 12, having an IR Spectrum as shown in FIG. 2.

16. Dexrabeprazole magnesium hydrate according to claim 2, having an X-ray diffraction pattern as shown in FIG. 1.

17. Dexraheprazole magnesium hydrate according to claim 2, having an IR Spectrum as shown in FIG. 2.

18. Dexrabeprazole magnesium hydrate according to claim 4, in crystalline form and being characterized by having an X-ray diffraction pattern with peaks at 4.3°, 6.2° and 9.9° 2θ±0.2° 2θ.

19. Dexrabeprazole magnesium hydrate according to claim 5, in crystalline form and being characterized by having an X-ray diffraction pattern with peaks at 4.3°, 6.2° and 9.9° 2θ±0.2° 2θ.

20. Dexrabeprazole magnesium hydrate according to claim 4, having an IR Spectrum as shown in FIG. 2.

21. Dexrabeprazole magnesium hydrate according to claim 1, having an X-ray diffraction pattern as shown in FIG. 1 and having an IR Spectrum as shown in FIG. 2.

22. Dexrabeprazoie magnesium hydrate according to claim 2, having an X-ray diffraction pattern as shown in FIG. 1 and having an IR Spectrum as shown in FIG. 2.

* * * * *

UNITED STATES PATENT AND TRADEMARK OFFICE
CERTIFICATE OF CORRECTION

PATENT NO. : 8,912,337 B2
APPLICATION NO. : 13/805235
DATED : December 16, 2014
INVENTOR(S) : Dharmaraj Ramachandra Rao et al.

It is certified that error appears in the above-identified patent and that said Letters Patent is hereby corrected as shown below:

In the Claims:

Column 12, Line 33, replace "Dexrabeprazoie" with --Dexrabeprazole--.

Signed and Sealed this
Thirty-first Day of March, 2015

Michelle K. Lee
*Director of the United States Patent and Trademark Office*